United States Patent [19]
de Nanteuil et al.

[11] Patent Number: 5,972,968
[45] Date of Patent: Oct. 26, 1999

[54] BENZIMIDAZOLE, BENZOXAZOLE AND BENZOTHIAZOLE COMPOUNDS

[75] Inventors: Guillaume de Nanteuil, Suresnes; Bernard Portevin, Elancourt; Jacqueline Bonnet, Paris; Armel Fradin, Neuilly sur Seine, all of France

[73] Assignee: Adir et Compagnie, Courbevoie, France

[21] Appl. No.: 08/899,288

[22] Filed: Jul. 23, 1997

[30] Foreign Application Priority Data

Jul. 26, 1996 [FR] France ................... 96 09416

[51] Int. Cl.⁶ .................. A61K 31/415; A61K 31/44; A61K 31/47; C07D 401/12
[52] U.S. Cl. ............ 514/338; 514/312; 514/333; 514/394; 546/153; 546/256; 546/273.4; 548/304.4; 548/309.7; 548/310.1; 548/310.4
[58] Field of Search ............... 546/256, 273.4; 514/333, 338

[56] References Cited

U.S. PATENT DOCUMENTS 4,430,502  2/1984  Nelson .................. 544/354
5,141,950  8/1992  Nakane et al. .......... 514/395

FOREIGN PATENT DOCUMENTS 02306916  12/1990  Japan .

*Primary Examiner*—Laura L. Stockton
*Attorney, Agent, or Firm*—The Firm of Gordon W. Hueschen

[57] ABSTRACT

A compound of formula (I):

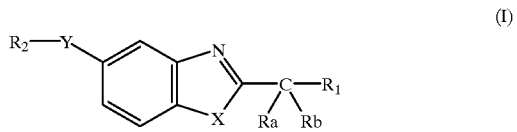

in which:

$R_1$ represents halogen or hydroxyl, alkoxy, trihalomethyl, amino, mercapto, alkylthio, trialkylammonium, aryloxy, arylthio, arylsulfonyl, arylsulfonyloxy, cycloalkyloxy, cycloalkylthio, bicycloalkyloxy or bicycloalkylthio, $R_a$ and $R_b$, which may be identical or different, represent hydrogen or alkyl, X represents oxygen or sulfur or NR, Y represents the group as defined in the description, $R_2$ represents an optionallly substituted aryl, its optical isomers as well as its addition salts with a pharmaceutically acceptable acid or base and medicinal products containing the same are useful as interleukin-1β inhibitor.

14 Claims, No Drawings

BENZIMIDAZOLE, BENZOXAZOLE AND BENZOTHIAZOLE COMPOUNDS

BACKGROUND OF THE INVENTION

These compositions, besides being new, are potent interleukin-1β (IL-1β) inhibitors.

DETAILED DESCRIPTION OF THE INVENTION

IL-1β is produced by macrophages, and possesses a wide variety of biological activities associated with inflammatory pathologies such as rheumatoid arthritis or osteoarthritis. IL-1β stimulates the cells present in the joint which synthesize and thus express inducible cyclooxygenase (COX2), as well as inducible NO synthase, to yield prostaglandins and NO which are important mediators of pain and inflammation. IL-1β also activates the expression and the synthesis of proteases which participate in the degradation of the extracellular matrix of the chondrocytes and in the abolition of the synthesis of the components of the cartilage matrix. Furthermore, IL-1β is involved in the activation of endothelial cells, which then express various adhesion factors, as well as in the induction of other proinflammatory cytokines such as TNF or chemokines (IL-6). Lastly, IL-1β plays a part in the regulation of bone resorption, as well as in differentiation and lymphocyte proliferation.

An IL-1β inhibitor can hence be expected to act against the inflammatory phenomena and to modify in a favorable manner the course of pathologies such as rheumatoid arthritis or osteoarthritis.

More specifically, the present invention relates to the compounds of formula (I):

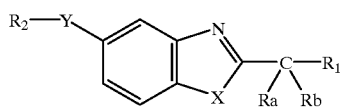

(I)

in which:
- $R_1$ represents a halogen atom, a hydroxyl, linear or branched ($C_1$–$C_6$) alkoxy (optionally substituted with an aryl group), trihalomethyl, amino (optionally substituted with one or more linear or branched ($C_1$–$C_6$) alkyl groups or optionally substituted aryl groups), mercapto, linear or branched ($C_1$–$C_6$) alkylthio, linear or branched ($C_1$–$C_6$) trialkylammonium, aryloxy, arylthio, arylsulfonyl, arylsulfonyloxy, ($C_3$–$C_7$) cycloalkyloxy or ($C_3$–$C_7$) cycloalkylthio group, a ($C_6$–$C_8$) bicycloalkyloxy group optionally substituted with an aryl group or a ($C_6$–$C_8$) bicycloalkylthio group optionally substituted with an aryl group,
- $R_a$ and $R_b$, which may be identical or different, represent a hydrogen atom or a linear or branched ($C_1$–$C_6$) alkyl group,
- X represents an oxygen or sulfur atom or a group NR (in which R represents a hydrogen atom or a linear or branched ($C_1$–$C_6$) alkyl group),
- Y represents —$(CH_2)_m$—Z—$(CH_2)_n$— wherein:
  - m is 0, 1 or 2,
  - n is 0, 1 or 2,
  - Z represents an oxygen or sulfur atom or an amino group (optionally substituted with a linear or branched ($C_1$–$C_6$) alkyl group) or an —$SO_2$—, —CHOH—, —$CH_2$— or —$CH(CH_2OH)$— group,
- $R_2$ represents an optionally substituted aryl group, their isomers as well as their addition salts with a pharmaceutically acceptable acid or base.

Among pharmaceutically acceptable acids, there may be mentioned, without implied limitation, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic, camphoric, and the like, acids.

Among pharmaceutically acceptable bases, there may be mentioned, without implied limitation, sodium hydroxide, potassium hydroxide, triethylamine, tert-butylamine, and the like.

Optionally substituted aryl group is understood to mean a mono- or bicyclic aromatic group optionally containing a nitrogen atom, optionally substituted with one or more halogen atoms or linear or branched ($C_1$–$C_6$) alkyl, linear or branched ($C_1$–$C_6$) trihaloalkyl, linear or branched ($C_1$–$C_6$) alkoxy, hydroxyl, nitro, cyano, amino (optionally substituted with one or more linear or branched ($C_1$–$C_6$) alkyl groups), substituted phenyl or substituted bicycloalkyl groups.

Among preferred aryl groups, the following groups, substituted or otherwise, may be mentioned: phenyl, naphthyl, pyridyl, quinolyl, imidazolyl or pyridyl N-oxide.

Preferred compounds of the invention are the compounds of formula (I) in which X represents a group —NR (in which R represents a hydrogen atom or a linear or branched ($C_1$–$C_6$) alkyl group).

Preferred groups $R_2$ according to the invention are phenyl and pyridyl groups, each of these groups being optionally substituted.

Preferred groups $R_1$ according to the invention are hydroxyl, mercapto, aryloxy and arylthio groups.

Preferred compounds according to the invention are the compounds of formula (I) in which Y represents an oxygen or sulfur atom or an eventually substituted amino group, The present invention also extends to the process for preparing the compounds of formula (I). When the compounds of formula (I) which it is desired to obtain are such that X=NR, the process is distinguished by the fact that a compound of formula (II):

(II)

in which $R_2$ and Y are as defined in the formula (I), is used as starting material, which is reacted with 2-nitro-5-chloroaniline,
to yield the compound of formula (III):

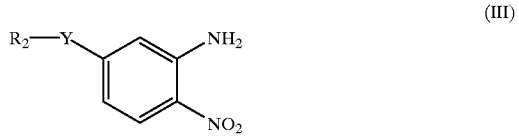

(III)

in which $R_2$ and Y are as defined in the formula (I), which undergoes a catalytic reduction, to yield the compound of formula (IV):

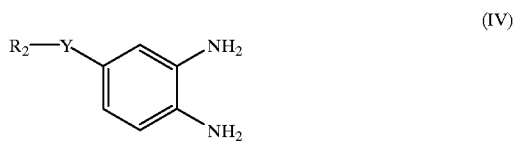

(IV)

in which $R_2$ and Y are as defined in the formula (I), which is reacted in an acid medium with a compound of formula (V):

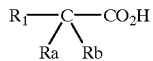
(V)

in which $R_a$, $R_b$ and $R_1$ have the same meaning as in the formula (I), to yield the compound of formula (I/a), a special case of the compounds of formula (I):

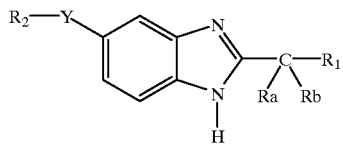
(I/a)

in which $R_1$, $R_a$, $R_b$, $R_2$ and Y are as defined in the formula (I), which undergoes, where appropriate, when $R_1$ represents a hydroxyl group, the action of thionyl chloride, to yield the compound of formula (I/b), a special case of the compounds of formula (I):

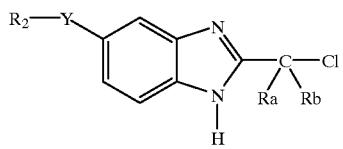
(I/b)

in which $R_2$, Y, $R_a$ and $R_b$ have the same meaning as in the formula (I), which can then undergo the standard reactions which can be carried out on chlorinated compounds, to obtain the corresponding substitutions;

which compound of formula (I/a) or (I/b):

can, where appropriate, undergo substitution of its NH function with a linear or branched ($C_1$–$C_6$) alkyl group, can be purified, if need be, according to a conventional purification technique, is separated, if need be, into its isomers according to a conventional separation technique, is converted, if so desired, to its addition salts with a pharmaceutically acceptable base.

The compounds of formula (III) described above can also be obtained by reacting a halogenated compound of formula $R_2$—Y-hal (such that $R_2$ and Y are as defined in the formula (I) and hal represents a halogen atom) with a hydroxynitroaniline.

When the compounds of formula (I) which it is desired to obtain are such that X=X'=O or S, the process is distinguished by the fact that a compound of formula (VI):

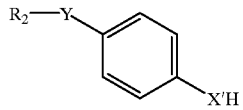
(VI)

in which $R_2$ and Y are as defined in the formula (I) and X' represents an oxygen or sulfur atom, is used as starting material, which is reacted with nitric acid,
to yield the compound of formula (VII):

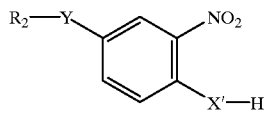
(VII)

in which $R_2$, Y and X' are as defined above, which undergoes a catalytic hydrogenation, to yield the compound of formula (VIII):

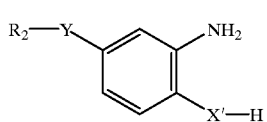
(VIII)

which is reacted in an acid medium with a compound of formula (V):

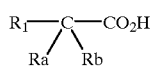
(V)

in which $R_a$, $R_b$ and $R_1$ have the same meaning as in the formula (I),
to yield the compound of formula (I/c), a special case of the compounds of formula (I):

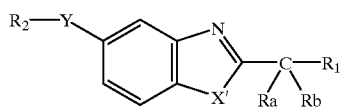
(I/c)

in which $R_2$, Y, X', $R_a$, $R_b$ and $R_1$ are as defined above, which undergoes, where appropriate, when $R_1$ represents a hydroxyl group, the action of thionyl chloride,
to yield the compound of formula (I/d), a special case of the compounds of formula (I):

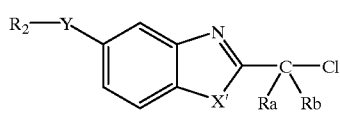
(I/d)

in which $R_2$, X', Y, $R_a$ and $R_b$ have the same meaning as above,
which can then undergo the standard reactions which can be carried out on chlorinated compounds, to obtain the corresponding substitutions;

which compound of formula (I/c) or (I/d):
- can be purified, if need be, according to a conventional purification technique,
- is separated, if need be, into its isomers according to a conventional separation technique,
- is converted, if so desired, to its addition salts with a pharmaceutically acceptable base.

The invention also extends to pharmaceutical compositions containing as active principle at least one compound of formula (I) with one or more suitable nontoxic, inert excipients. Among the pharmaceutical compositions according to the invention, there may be mentioned more especially those which are suitable for oral, parenteral (intravenous or subcutaneous), or nasal administration, simple or sugar-coated tablets, sublingual tablets, hard gelatin capsules, troches, suppositories, creams, ointments, skin gels, injectable preparations, suspensions to be swallowed, and the like.

The appropriate dosage can be adapted to suit the nature and severity of the complaint, the administration route and also the patient's age and weight. This dosage varies from 0.1 to 100 mg daily in one or more doses.

The examples which follow illustrate the invention but in no way limit it.

The starting materials used are known products or are prepared according to known procedures.

The structures of the compounds described in the examples and the preparations were determined according to standard spectrophotometric techniques (infrared, NMR, mass spectrometry, etc.).

EXAMPLE 1

2-Hydroxymethyl-5-(4-pyridyloxy)benzimidazole

Stage 1: 2-Amino-4-(4-pyridyloxy)nitrobenzene

A 2-liter round-bottomed flask is charged with 35.2 g (0.369 mol) of 4-hydroxypyridine and 250 ml of anhydrous dimethylformamide (DMF). Under nitrogen, 42 g (0.369 mol) of potassium tert-butylate are added portionwise while the temperature is maintained at 15–20° C. with a water/ice bath. After the addition, the mixture is stirred for 2 hours and a pale yellow solution is obtained. 60 g (0.358 mol) of 2-nitro-5-chloroaniline are then added and an intense red coloration is obtained. The mixture is brought to 100° C. for 6 hours and then allowed to cool overnight. The DMF is evaporated off and water is then added; a precipitate is obtained, which is filtered off and washed with isopropanol in the heated state and then dried.

Melting point: >260° C.

| Elemental microanalysis: | | | |
|---|---|---|---|
| | C % | H % | N % |
| calculated | 57.14 | 3.92 | 18.17 |
| found | 56.93 | 3.98 | 17.75 |

Stage 2: 2-Amino-4-(4-pyridyloxy)aniline 30 g (0.130 mol) of 2-amino-4-(4-pyridyloxy) nitrobenzene obtained in the preceding stage are suspended in 600 ml of a water/citric acid (50:50) mixture. 2 g of 10% palladium on charcoal are added and the mixture is hydrogenated for 18 h at 4 kg pressure and at room temperature. The catalyst is filtered off and the filtrate is evaporated. The residue is dissolved in water. This aqueous phase is alkalinized with potassium carbonate. The precipitate obtained is filtered off, washed with water and dried. The expected product is purified by chromatography on silica gel (eluent: CH$_2$Cl$_2$/MeOH, 80:20).

Melting point: 260° C.

| Elemental microanalysis: | | | |
|---|---|---|---|
| | C % | H % | N % |
| calculated | 65.66 | 5.51 | 20.88 |
| found | 65.78 | 5.54 | 20.79 |

Stage 3: 2-Hydroxymethyl-5-(4-pyridyloxy)benzimidazole

A 250-ml round-bottomed flask equipped with a stirrer and a condenser is charged with 3 g (14.9 mmol) of the compound obtained in the preceding stage, 30 ml of 4N hydrochloric acid and 2.1 g (50% excess) of glycolic acid. The mixture is brought to reflux for 6 hours and then allowed to cool. On alkalinization with 10N sodium hydroxide, the product precipitates and is filtered off, washed with 3 times 30 ml of water and dried in a desiccator. The product is purified by chromatography on silica gel (eluent: CHCl$_2$/MeOH/NH$_2$OH, 80:20:1).

Melting point: 250° C.

| Elemental microanalysis: | | | |
|---|---|---|---|
| | C % | H % | N % |
| calculated | 64.72 | 4.60 | 17.42 |
| found | 64.60 | 5.04 | 17.35 |

EXAMPLE 2

2-Chloromethyl-5-(4-pyridyloxy)benzimidazole dihydrochloride

A 250-ml round-bottomed flask equipped with a stirrer and a condenser is charged with 3.18 g (13.2 mmol) of 2-hydroxymethyl-5-(4-pyridyloxy)benzimidazole obtained in Example 1 and 40 ml of thionyl chloride. The mixture is brought to reflux for 2 hours and then cooled. The precipitate is filtered off, washed with ether and dried, and yields the expected product.

Melting point: >250° C.

| Elemental microanalysis: | | | | |
|---|---|---|---|---|
| | C % | H % | N % | Cl % | Cl⁻ % |
| calculated | 46.94 | 3.64 | 12.63 | 31.98 | 21.32 |
| found | 46.13 | 3.62 | 12.09 | 32.04 | 21.06 |

EXAMPLE 3

2-Hydroxymethyl-5-phenoxybenzimidazole

Stage 1: 2-Amino-4-phenoxynitrobenzene

The expected product is obtained according to the process described in Stage 1 of Example 1, replacing 4-hydroxypyridine by phenol.

Melting point: 150° C.

Stage 2: 2-Amino-4-phenoxyaniline 23.6 g (0.109 mol) of 2-amino-4-phenoxynitrobenzene obtained in the preceding stage are dissolved in 550 ml of dioxane. After hydrogenation (H$_2$/Pd) for 18 h at room temperature and at 4 kg pressure, the catalyst is filtered off and the filtrate is evaporated. The residue is taken up with pentane, filtered and dried, and yields the expected product.

Melting point: 72° C.

Stage 3: 2-Hydroxymethyl-5-phenoxybenzimidazole 19.4 g (97 mmol) of the compound obtained in the preceding stage, 155 ml of 4N HCl and 14.2 g (50% excess) of glycolic acid are brought to reflux for 5 hours with stirring. The mixture is allowed to cool. The hydrochloride of the expected product precipitates, and is filtered off, rinsed with water and dried.

Melting point: 220° C.

Elemental microanalysis:

|  | C % | H % | N % | Cl % | Cl⁻ % |
|---|---|---|---|---|---|
| calculated | 60.77 | 4.73 | 10.12 | 12.81 | 12.81 |
| found | 60.67 | 4.76 | 10.07 | 12.81 | 12.98 |

On alkalinization of the hydrochloride with 10N sodium hydroxide, and after filtration, washing with water and drying, the expected product is recovered in free base form.

Melting point: 200° C.

EXAMPLE 4

2-Chloromethyl-5-phenoxybenzimidazole hydrochloride 3.6 g (15 mmol) of the compound described in Example 3, 60 ml of toluene and 8 ml of thionyl chloride are brought to reflux for 1 h 30 min. After filtration and drying, the expected product is obtained.

Melting point: 172° C.

Elemental microanalysis:

|  | C % | H % | N % | Cl % | Cl⁻ % |
|---|---|---|---|---|---|
| calculated | 56.97 | 4.10 | 9.49 | 24.02 | 12.01 |
| found | 56.06 | 4.08 | 9.30 | 23.86 | 11.92 |

EXAMPLE 5

(5-Phenoxy-2-benzimidazolyl) methyltrimethylammonium chloride 2 g (6.8 mmol) of the compound described in Example 4 are suspended in 100 ml of acetone. 6.6 g of a 33% solution of trimethylamine in ethanol are added. The medium solubilizes instantaneously. After stiring overnight at room temperature, the mixture is evaporated. The residue is purified on a Biogel column (CH₃CN/H₂O, 50:50) and then crystallized in acetone. The expected product is obtained after filtration and drying.

Melting point: 238–240° C.

Elemental microanalysis:

|  | C % | H % | N % | Cl⁻ % |
|---|---|---|---|---|
| calculated | 64.25 | 6.34 | 13.22 | 11.16 |
| found | 64.19 | 6.49 | 12.86 | 11.02 |

The examples which follow were obtained according to the process described in Example 3, from the corresponding starting materials.

EXAMPLE 6

2-Mercaptomethyl-5-phenoxybenzimidazole

From mercaptoethanoic acid.

Melting point: 168° C.

Elemental microanalysis:

|  | C % | H % | N % | Cl % | S % |
|---|---|---|---|---|---|
| calculated | 57.43 | 4.48 | 9.57 | 12.11 | 10.95 |
| found | 57.27 | 4.53 | 9.27 | 12.40 | 10.49 |

EXAMPLE 7

2-Aminomethyl-5-phenoxybenzimidazole

From glycine.

Melting point: 123° C.

Elemental microanalysis:

|  | C % | H % | N % |
|---|---|---|---|
| calculated | 70.28 | 5.48 | 17.56 |
| found | 69.96 | 5.67 | 17.26 |

EXAMPLE 8

2-(Trifluoromethyl)methyl-5-phenoxybenzimidazole

From trifluoromethylethanoic acid.

Melting point: 188° C.

EXAMPLE 9

2-Methoxymethyl-5-phenoxybenzimidazole

From methoxyethanoic acid.

Melting point: 74° C.

Elemental microanalysis:

|  | C % | H % | N % |
|---|---|---|---|
| calculated | 70.85 | 5.55 | 11.02 |
| found | 70.93 | 5.85 | 10.89 |

EXAMPLE 10

2-Tosyloxymethyl-5-phenoxybenzimidazole

By reacting the compound described in Example 3 with tosyl chloride.

Melting point: 138° C.

Elemental microanalysis:

|  | C % | H % | N % | S % |
|---|---|---|---|---|
| calculated | 63.95 | 4.60 | 7.10 | 8.13 |
| found | 64.02 | 4.67 | 7.09 | 7.98 |

EXAMPLE 11

2-(2-Hydroxy-2-propyl)-5-phenoxybenzimidazole

Melting point: 186° C.

| | Elemental microanalysis: | | |
|---|---|---|---|
| | C % | H % | N % |
| calculated | 71.62 | 6.01 | 10.44 |
| found | 71.96 | 6.11 | 10.28 |

EXAMPLE 12

2-Hydroxymethyl-5-(4-aminophenoxy) benzimidazole dihydrochloride

Melting point: >250° C.

| | Elemental microanalysis: | | | |
|---|---|---|---|---|
| | C % | H % | N % | Cl % |
| calculated | 51.24 | 4.61 | 12.80 | 21.60 |
| found | 51.02 | 4.99 | 12.26 | 21.01 |

EXAMPLE 13

5-(1-Phenyl-1-aminomethyl)-2-(hydroxymethyl) benzimidazole dihydrochloride

Melting point: 200° C.

| | Elemental microanalysis: | | | |
|---|---|---|---|---|
| | C % | H % | N % | Cl % |
| calculated | 55.23 | 5.25 | 12.88 | 21.74 |
| found | 55.82 | 5.39 | 12.74 | 22.58 |

EXAMPLE 14

5-(1-Phenyl-1-hydroxymethyl)-2-(hydroxymethyl) benzimidazole hydrochloride

Melting point: >260° C.

| | Elemental microanalysis: | | | |
|---|---|---|---|---|
| | C % | H % | N % | Cl % |
| calculated | 61.97 | 5.20 | 9.63 | 12.19 |
| found | 62.04 | 5.27 | 9.52 | 12.66 |

EXAMPLE 15

2-Hydroxymethyl-5-(4-pyridylthio)benzimidazole dihydrochloride

Melting point: >260° C.

| | Elemental microanalysis: | | | | |
|---|---|---|---|---|---|
| | C % | H % | N % | Cl % | S % |
| calculated | 47.28 | 3.97 | 12.72 | 21.47 | 9.71 |
| found | 47.16 | 3.92 | 12.24 | 21.65 | 9.93 |

EXAMPLE 16

2-Hydroxymethyl-5-(3-pyridyloxy)benzimidazole dihydrochloride

Melting point: 185° C.

| | Elemental microanalysis: | | | |
|---|---|---|---|---|
| | C % | H % | N % | Cl % |
| calculated | 49.70 | 4.17 | 13.37 | 22.57 |
| found | 49.30 | 4.97 | 13.05 | 22.59 |

EXAMPLE 17

2-Hydroxymethyl-5-(2-pyridylthio)benzimidazole dihydrochloride

Melting point: 190° C.

| | Elemental microanalysis: | | | | |
|---|---|---|---|---|---|
| | C % | H % | N % | Cl % | S % |
| calculated | 47.28 | 3.97 | 12.72 | 21.47 | 9.71 |
| found | 46.95 | 4.05 | 12.63 | 21.67 | 9.96 |

EXAMPLE 18

2-Phenoxymethyl-5-(4-pyridylthio)benzimidazole dihydrochloride

Melting point: 160° C.

| | Elemental microanalysis: | | | | |
|---|---|---|---|---|---|
| | C % | H % | N % | Cl % | S % |
| calculated | 56.16 | 4.22 | 10.34 | 17.45 | 7.89 |
| found | 57.27 | 4.09 | 10.31 | 17.58 | 7.89 |

EXAMPLE 19

2-Hydroxymethyl-5-[(7-trifluoromethyl-4-quinolyl)thio]benzimidazole

Melting point: 242° C.

| | Elemental microanalysis: | | | |
|---|---|---|---|---|
| | C % | H % | N % | S % |
| calculated | 57.60 | 3.22 | 11.19 | 8.54 |
| found | 57.68 | 3.54 | 10.80 | 8.21 |

EXAMPLE 20

2-Hydroxymethyl-5-[(2-imidazolyl)thio]benzimidazole dihydrochloride

Melting point: >260° C.

| | Elemental microanalysis: | | | | |
|---|---|---|---|---|---|
| | C % | H % | N % | Cl % | S % |
| calculated | 41.39 | 3.79 | 17.55 | 22.21 | 10.04 |
| found | 41.36 | 3.88 | 17.08 | 22.45 | 10.05 |

EXAMPLE 21

2-(4-Pyridylthiomethyl)-5-(4-pyridylthio)benzimidazole trihydrochloride

Melting point: >260° C.

| | Elemental microanalysis: | | | | |
|---|---|---|---|---|---|
| | C % | H % | N % | Cl % | S % |
| calculated | 47.01 | 3.73 | 12.19 | 23.13 | 13.93 |
| found | 47.31 | 4.01 | 12.16 | 23.27 | 14.10 |

EXAMPLE 22

2-Phenylthiomethyl-5-(4-pyridylthio)benzimidazole dihydrochloride

Melting point: 168° C.

| | Elemental microanalysis: | | | | |
|---|---|---|---|---|---|
| | C % | H % | N % | Cl % | S % |
| calculated | 54.03 | 4.06 | 9.95 | 16.79 | 15.18 |
| found | 53.61 | 4.24 | 9.71 | 17.28 | 14.82 |

EXAMPLE 23

2-Hydroxymethyl-5-(3-pyridylthio)benzimidazole dihydrochloride

Melting point: 260° C.

| | Elemental microanalysis: | | | | |
|---|---|---|---|---|---|
| | C % | H % | N % | Cl % | S % |
| calculated | 47.28 | 3.97 | 12.72 | 21.47 | 9.71 |
| found | 46.41 | 3.86 | 12.34 | 22.57 | 9.58 |

EXAMPLE 24

2-(4-Chlorophenoxymethyl)-5-(4-pyridylthio)benzimidazole dihydrochloride

Melting point: 198° C.

| | Elemental microanalysis: | | | | |
|---|---|---|---|---|---|
| | C % | H % | N % | Cl % | S % |
| calculated | 51.77 | 3.66 | 9.53 | 24.13 | 7.27 |
| found | 52.43 | 3.71 | 9.60 | 24.24 | 6.93 |

EXAMPLE 25

2-(Phenylsulfonylmethyl)-5-(4-pyridylthio)benzimidazole dihydrochloride

| | Elemental microanalysis: | | | | |
|---|---|---|---|---|---|
| | C % | H % | N % | Cl % | S % |
| calculated | 50.22 | 3.77 | 9.25 | 15.60 | 14.11 |
| found | 50.54 | 3.97 | 9.22 | 16.09 | 14.17 |

EXAMPLE 26

2-Phenoxymethyl-5-(4-pyridylsulfonyl N-oxide)benzimidazole

Melting point: 210° C.

| | Elemental microanalysis: | | | |
|---|---|---|---|---|
| | C % | H % | N % | S % |
| calculated | 59.83 | 3.96 | 11.02 | 8.41 |
| found | 59.68 | 3.99 | 11.04 | 8.13 |

EXAMPLE 27

2-Phenoxymethyl-5-(4-pyridylsulfonyl)benzimidazole dihydrochloride

Melting point: 174° C.

| | Elemental microanalysis: | | | | |
|---|---|---|---|---|---|
| | C % | H % | N % | Cl % | S % |
| calculated | 52.06 | 3.92 | 9.59 | 16.18 | 7.31 |
| found | 52.27 | 4.01 | 9.30 | 15.44 | 6.64 |

EXAMPLE 28

2-Benzyloxymethyl-5-(4-pyridylthio)benzimidazole

| | Elemental microanalysis: | | | |
|---|---|---|---|---|
| | C % | H % | N % | S % |
| calculated | 69.14 | 4.93 | 12.09 | 9.23 |
| found | 69.43 | 4.92 | 12.08 | 9.62 |

EXAMPLE 29

2-(2-Naphthyloxymethyl)-5-(4-pyridylthio) benzimidazole

| | Elemental microanalysis: | | | |
|---|---|---|---|---|
| | C % | H % | N % | S % |
| calculated | 72.04 | 4.47 | 10.96 | 8.30 |
| found | 72.26 | 4.41 | 11.00 | 8.30 |

EXAMPLE 30

2-(1-Naphthyloxymethyl)-5-(4-pyridylthio) benzimidazole

| | Elemental microanalysis: | | | |
|---|---|---|---|---|
| | C % | H % | N % | S % |
| calculated | 72.04 | 4.47 | 10.96 | 8.36 |
| found | 72.46 | 4.41 | 10.80 | 8.57 |

EXAMPLE 31

2-Phenoxymethyl-5-(N-methyl-4-pyridylamino) benzimidazole dihydrochloride

| | Elemental microanalysis: | | | |
|---|---|---|---|---|
| | C % | H % | N % | Cl % |
| calculated | 59.56 | 5.00 | 13.89 | 17.58 |
| found | 59.32 | 5.01 | 13.79 | 18.61 |

EXAMPLE 32

2-Phenoxymethyl-5-(3-pyridylthio)benzimidazole

Melting point: 118° C.

| | Elemental microanalysis: | | | |
|---|---|---|---|---|
| | C % | H % | N % | S % |
| calculated | 68.45 | 4.53 | 12.60 | 9.62 |
| found | 68.77 | 4.60 | 12.68 | 9.82 |

EXAMPLE 33

2-Phenoxymethyl-5-[(RS)-α-hydroxybenzyl] benzimidazole

| | Elemental microanalysis: | | |
|---|---|---|---|
| | C % | H % | N % |
| calculated | 76.34 | 5.49 | 8.48 |
| found | 76.04 | 5.54 | 8.29 |

EXAMPLE 34

2-Hydroxymethyl-5-(4-pyridylamino)benzimidazole dihydrochloride

Melting point: >250° C.

| | Elemental microanalysis: | | | |
|---|---|---|---|---|
| | C % | H % | N % | Cl % |
| calculated | 49.86 | 4.54 | 17.89 | 22.64 |
| found | 49.89 | 4.56 | 17.87 | 22.42 |

Examples 35 to 37 were synthesized according to the process described in Example 3, by reacting 5-hydroxy-2-nitroaniline in Stage 1 with the corresponding halogenated compound.

EXAMPLE 35

2-Hydroxymethyl-5-(4-pyridyloxy)benzimidazole dihydrochloride

Melting point: 220° C.

| | Elemental microanalysis: | | | |
|---|---|---|---|---|
| | C % | H % | N % | Cl % |
| calculated | 49.70 | 4.17 | 13.37 | 22.57 |
| found | 49.51 | 4.31 | 13.22 | 22.81 |

EXAMPLE 36

2-Phenoxymethyl-5-(4-pyridylmethoxy) benzimidazole

Melting point: 162° C.

| | Elemental microanalysis: | | |
|---|---|---|---|
| | C % | H % | N % |
| calculated | 72.49 | 5.17 | 12.68 |
| found | 72.34 | 5.32 | 12.69 |

EXAMPLE 37

2-Hydroxymethyl-5-(4-pyridylmethoxy)benzimidazole dihydrochloride

Melting point: >260° C.

| Elemental microanalysis: | | | | |
|---|---|---|---|---|
| | C % | H % | N % | Cl % |
| calculated | 51.24 | 4.61 | 12.80 | 21.60 |
| found | 51.19 | 5.09 | 12.88 | 21.49 |

EXAMPLE 38

2-Phenoxymethyl-5-(4-pyridylmethyl)benzimidazole dihydrochloride

The expected compound was synthesized according to the process described in Example 3, Stages 2 and 3, using 2-nitro-4-(4-pyridylmethyl)aniline in Stage 2.

Melting point: 160° C.

| Elemental microanalysis: | | | | |
|---|---|---|---|---|
| | C % | H % | N % | Cl % |
| calculated | 61.87 | 4.93 | 10.82 | 18.26 |
| found | 62.03 | 5.08 | 10.87 | 18.62 |

Examples 39 and 40 were obtained by methylation of the compound of Example 3, followed by separation by chromatography on a silica column.

EXAMPLE 39

1-Methyl-2-hydroxymethyl-5-phenoxybenzimidazole hydrochloride

Melting point: 194° C.

| Elemental microanalysis: | | | | |
|---|---|---|---|---|
| | C % | H % | N % | Cl % |
| calculated | 61.97 | 5.20 | 9.63 | 12.19 |
| found | 61.88 | 5.22 | 9.54 | 12.01 |

EXAMPLE 40

3-Methyl-2-hydroxymethyl-5-phenoxybenzimidazole hydrochloride

Melting point: 164° C.

| Elemental microanalysis: | | | | |
|---|---|---|---|---|
| | C % | H % | N % | Cl % |
| calculated | 61.97 | 5.20 | 9.63 | 12.19 |
| found | 62.05 | 5.06 | 9.60 | 12.28 |

The compounds of the examples which follow were prepared from the corresponding starting materials.

EXAMPLE 41

2-Phenoxymethyl-5-(4-pyridylthiomethyl)benzimidazole

EXAMPLE 42

2-Cyclohexyloxymethyl-5-(4-pyridylthio)benzimidazole

EXAMPLE 43

2-(4-Chlorophenoxy)methyl-5-(4-pyridylthio)benzimidazole

EXAMPLE 44

2-(3,4-Dichlorophenoxy)methyl-5-(4-pyridylthio)benzimidazole

EXAMPLE 45

2-(2,4-Dichlorophenoxy)methyl-5-(4-pyridylthio)benzimidazole

EXAMPLE 46

2-(4-Methoxyphenoxy)methyl-5-(4-pyridylthio)benzimidazole

EXAMPLE 47

2-(4-Fluorophenoxy)methyl-5-(4-pyridylthio)benzimidazole

EXAMPLE 48

2-(3,4,5-Trimethoxyphenoxy)methyl-5-(4-pyridylthio)benzimidazole

EXAMPLE 49

2-(2,6-Dimethoxyphenoxy)methyl-5-(4-pyridylthio)benzimidazole

EXAMPLE 50

2-[3-(Trifluoromethyl)phenoxy]methyl-5-(4-pyridylthio)benzimidazole

EXAMPLE 51

2-[3,5-Bis(trifluoromethyl)phenoxy]methyl-5-(4-pyridylthio)benzimidazole

EXAMPLE 52

2-(4-Phenylphenoxy)methyl-5-(4-pyridylthio)benzimidazole

EXAMPLE 53

2-[4-(4-Methylphenyl)bicyclo[2.2.2]oct-1-yloxy]methyl-5-(4-pyridylthio)benzimidazole

EXAMPLE 54

2-[4-(4-Methoxybicyclo[2.2.2]oct-1-yl)phenoxy]methyl-5-(4-pyridylthio)benzimidazole

EXAMPLE 55

2-Phenylthiomethyl-5-(3-pyridylthio)benzimidazole

EXAMPLE 56

2-Phenylsulfonylmethyl-5-(4-pyridylthio)benzimidazole

EXAMPLE 57

2-(4-Pyridyloxy)methyl-5-(4-pyridylthio)benzimidazole

EXAMPLE 58

2-Phenoxymethyl-5-(1-phenyl-1-hydroxymethyl)benzimidazole

EXAMPLE 59

2-(4-Pyridyloxy)methyl-5-(1-phenyl-1-hydroxymethyl)benzimidazole

EXAMPLE 60

2-Phenoxymethyl-5-[1-(3-pyridyl)-2-hydroxyethyl]benzimidazole

EXAMPLE 61

2-(4-Pyridyloxy)methyl-5-[1-(3-pyridyl)-2-hydroxyethyl]benzimidazole

EXAMPLE 62

2-Phenoxymethyl-5-[(3-pyridyl)methylthiomethyl]benzimidazole

EXAMPLE 63

2-Phenoxymethyl-5-[2-(3-pyridyl)ethoxy]benzimidazole

EXAMPLE 64

2-Phenoxymethyl-5-[4-(dimethylamino)phenoxy]benzimidazole

EXAMPLE 65

2-Phenoxymethyl-5-[(3-pyridyl)thio]benzimidazole

EXAMPLE 66

Pharmacological study of the compounds of the invention

The compounds were studied on the monocyte/macrophage type human cell line THP1. The production of IL-1β by these cells was obtained after stimulation with bacterial lipopolysaccharide (M. Turner et coll., *Biochem. Biophys. Res. Comm.*, 1988, 256(2), 830–839) and assayed by the EIA method (Cayman kit) according to the instructions supplied by the manufacturer. In the test of endotoxic shock induced in mice by intravenous injection of lipopolysaccharide, the compounds of the invention decreased the circulating levels of TNFα by approximately 50% for an oral dose of 100 mg/kg.

EXAMPLE 67

Pharmaceutical Composition

Preparation formula for 1000 tablets containing a dose of 10 mg
Compound of Example 2 . . . 10 g
Hydroxypropylcellulose . . . 2 g
Wheat starch . . . 10 g
Lactose . . . 100 g
Magnesium stearate . . . 3 g
Talc . . . 3 g

We claim:

1. A compound selected from those of formula (I):

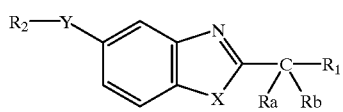

(I)

in which:

$R_1$ represents halogen, hydroxyl, linear or branched ($C_1$–$C_6$) alkoxy optionally substituted with an aryl group, trihalomethyl, amino optionally substituted with one or more linear or branched ($C_1$–$C_6$) alkyl groups or optionally substituted aryl groups, mercapto, linear or branched ($C_1$–$C_6$) alkylthio, linear or branched ($C_1$–$C_6$) trialkylammonium, aryloxy, arylthio, arylsulfonyl, arylsulfonyloxy, ($C_3$–$C_7$) cycloalkyloxy or ($C_3$–$C_7$) cycloalkylthio, ($C_6$–$C_8$) bicycloalkyloxy optionally substituted with aryl or ($C_6$–$C_8$) bicycloalkylthio optionally substituted with aryl, wherein each aryl means pyridyl or phenyl, $R_a$ and $R_b$, which may be identical or different, represent hydrogen or linear or branched ($C_1$–$C_6$) alkyl, X represents a group NR in which R represents a hydrogen atom or a linear or branched ($C_1$–$C_6$) alkyl group, Y represents —(CH$_2$)$_m$—Z—(CH$_2$)$_n$— wherein:
m is 0, 1 or 2,
n is 0, 1 or 2,
Z represents sulfur linear or branched ($C_1$–$C_6$) alkyl substituted with a linear or branched ($C_1$–$C_6$) alkyl or —SO$_2$—, —CHOH—, or —CH(CH$_2$OH)—, a pyridine ring being present in at least one of $R_1$ and $R_2$, $R_2$ represents optionally substituted pyridyl or phenyl, or an optical isomer or a pharmaceutically acceptable salt thereof.

2. The compound of claim 1, wherein Y represents a sulfur atom.

3. A compound of claim 1, wherein $R_1$ represents hydroxyl.

4. A compound of claim 1, wherein $R_1$ represents mercapto.

5. A compound of claim 1, wherein $R_1$ represents optionally substituted arylthio or aryloxy wherein aryl is pyridyl or phenyl.

6. A compound of claim 5, wherein $R_1$ represents optionally substituted phenoxy or phenylthio.

7. A compound of claim 1, wherein $R_2$ represents optionally substituted phenyl.

8. A compound of claim 1, wherein $R_2$ represents optionally substituted pyridyl.

9. The compound of claim 1, which is 2-phenoxymethyl 5-(4-pyridylthio)benzimidazole.

10. The compound claim 1, which is 2-phenoxymethyl-5-(N-methyl-4-pyridylamino)benzimidazole.

11. A pharmaceutical composition useful as an interleukin-1β inhibitor comprising as active principle an effective amount of a compound as claimed in claim 1, together with one or more pharmaceutically-acceptable excipients or vehicles.

12. A pharmaceutical composition useful as an interleukin-1β inhibitor comprising as active principle an effective amount of the compound of claim 10, together with one or more pharmaceutically-acceptable excipients or vehicles.

13. A method for treating a living body afflicted with a condition requiring an interleukin-1β inhibitor comprising the step of administering to the living body an amount of a compound of claim 1 which is effective for alleviation of said condition.

14. A method for treating a living body afflicted with a condition requiring an interleukin-1β inhibitor comprising the step of administering to the living body an amount of a compound of claim 10 which is effective for alleviation of said condition.

* * * * *

UNITED STATES PATENT AND TRADEMARK OFFICE
CERTIFICATE OF CORRECTION

PATENT NO. : 5,972,968
DATED : Oct. 26, 1999
INVENTOR(S) : G. de Nanteuil, B. Portevin, J. Bonnet, A. Fradin It is certified that error appears in the above-identified patent and that said Letters Patent is hereby corrected as shown below:

Column 7, line 50: "stiring" should read -- stirring --.

Column 18, line 13: Delete the following: "linear or branched $(C_1-C_6)$ alkyl substituted with a linear or branched $(C_1-C_6)$ alkyl".
    dtd 4/20/99, Claim 1, lines Column 18, line 20: Insert a -- - -- (hyphen) between "pharmaceutically" and "acceptable".
    Claim 1, line 21 (last line on the claim.

Column 18, line 22: "The" should be changed to -- A --.
    line 1

Signed and Sealed this

Second Day of May, 2000

Attest:

Q. TODD DICKINSON

*Attesting Officer*      *Director of Patents and Trademarks*